United States Patent
Onouchi et al.

(10) Patent No.: US 12,405,231 B2
(45) Date of Patent: Sep. 2, 2025

(54) RADIOGRAPHIC IMAGING APPARATUS AND RADIATION DETECTOR

(71) Applicant: FUJIFILM Healthcare Corporation, Kashiwa (JP)

(72) Inventors: Masafumi Onouchi, Kashiwa (JP); Takafumi Ishitsu, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 263 days.

(21) Appl. No.: 17/884,349

(22) Filed: Aug. 9, 2022

(65) Prior Publication Data

US 2023/0076183 A1    Mar. 9, 2023

(30) Foreign Application Priority Data

Sep. 8, 2021  (JP) .................................. 2021-146032

(51) Int. Cl.
    *G01N 23/046*    (2018.01)
    *A61B 6/40*      (2024.01)
    (Continued)

(52) U.S. Cl.
    CPC ............ *G01N 23/046* (2013.01); *A61B 6/40* (2013.01); *A61B 6/4241* (2013.01);
    (Continued)

(58) Field of Classification Search
    CPC ........... G01N 23/046; G01N 2223/304; G01N 2223/316; G01N 2223/501;
    (Continued)

(56) References Cited

U.S. PATENT DOCUMENTS

2018/0321395 A1    11/2018  Steadman Booker et al.
2019/0377096 A1*   12/2019  Bouhnik ................ G01T 1/247

FOREIGN PATENT DOCUMENTS

DE    102012202500 A1 *  8/2013  .......... A61B 6/4233
JP    2002-311145 A      10/2002
(Continued)

OTHER PUBLICATIONS

Translation of DE-102012202500-A1 (Year: 2013).*
(Continued)

*Primary Examiner* — David P Porta
*Assistant Examiner* — Mamadou Faye
(74) *Attorney, Agent, or Firm* — Paul Teng

(57) ABSTRACT

A radiographic imaging apparatus and a radiation detector are provided, which are capable of sufficiently reducing the sensitivity difference between pixels even if the incident photon rate is high. A radiographic imaging apparatus includes: a radiation source for irradiating an object with radiation; a plurality of detection element modules each having a semiconductor layer that generates electrical charges depending on photon energy of the radiation, and a photon counting circuit for counting the electrical charges for each pixel; and a collimator that is disposed between the radiation source and the semiconductor layer, and has a plurality of walls forming a plurality of passage holes through which the radiation passes. A plurality of subpixels is formed on the semiconductor layer, and when one or more subpixels defined by the walls of the collimator are grouped as a macro pixel, a plurality of macro pixels arranged from each end of each of the detection element modules is smaller in size than a macro pixel other than the plurality of macro pixels arranged from the end of the detection element module.

16 Claims, 10 Drawing Sheets

(51) Int. Cl.
*A61B 6/42* (2024.01)
*H10F 39/00* (2025.01)
(52) U.S. Cl.
CPC ... *H10F 39/8023* (2025.01); *G01N 2223/304* (2013.01); *G01N 2223/316* (2013.01); *G01N 2223/501* (2013.01); *G01N 2223/612* (2013.01)
(58) Field of Classification Search
CPC .. G01N 2223/612; A61B 6/40; A61B 6/4241; A61B 6/06; H01L 27/14605
See application file for complete search history.

(56) References Cited

FOREIGN PATENT DOCUMENTS

| | | | |
|---|---|---|---|
| JP | 2009-025149 A | 2/2009 | |
| JP | 2019-504297 A | 2/2019 | |

OTHER PUBLICATIONS

Japanese official action dated Oct. 24, 2023 (and machine translation) in connection with Japanese Patent Application No. 2021-146032.

\* cited by examiner

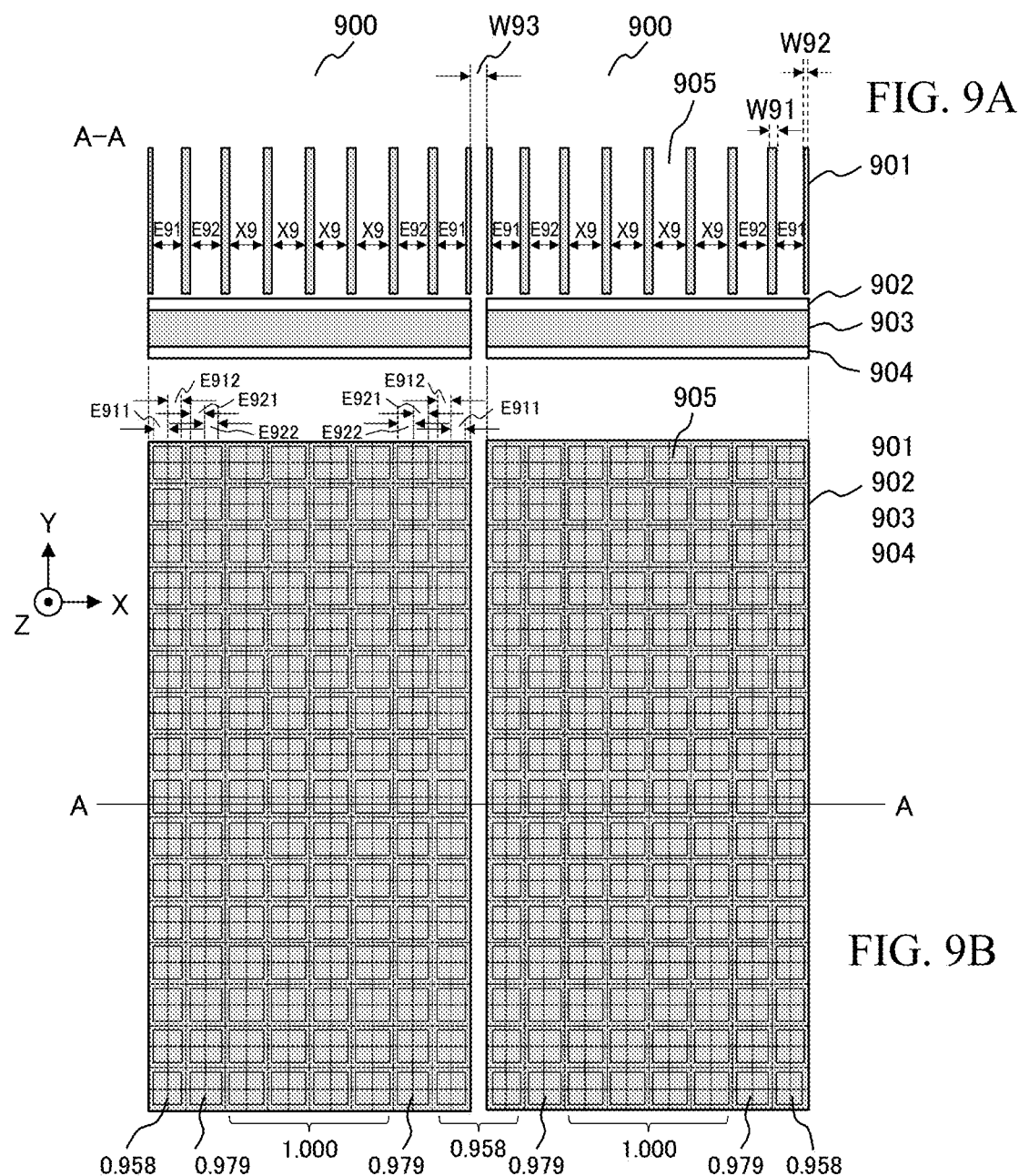
FIG. 9A
FIG. 9B
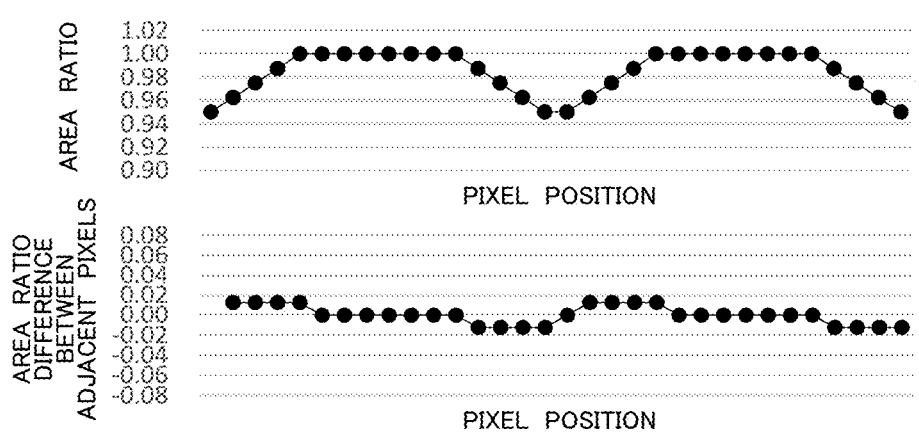
FIG. 9C
FIG. 9D

FIG. 10A
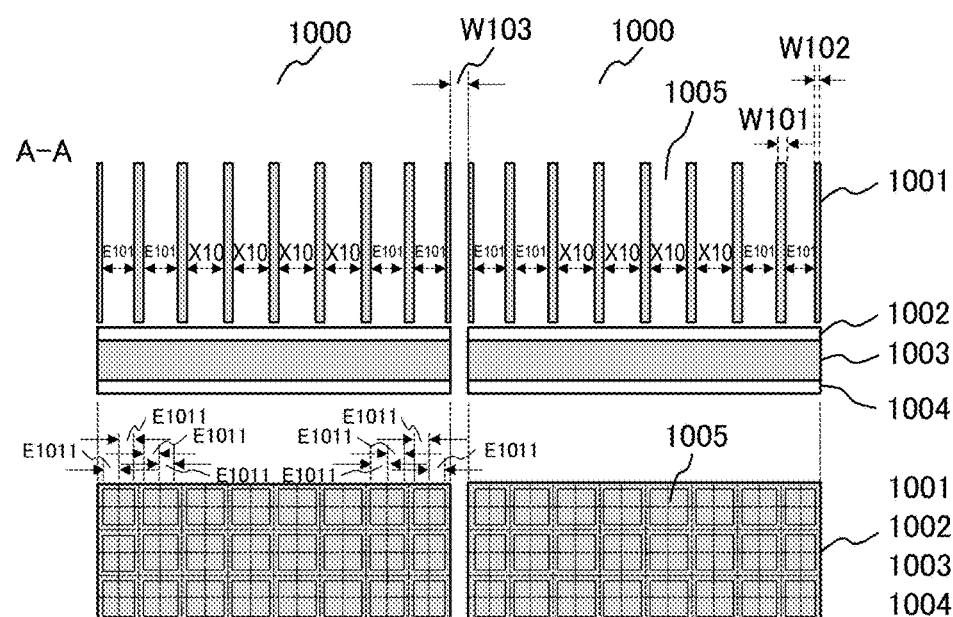
FIG. 10B
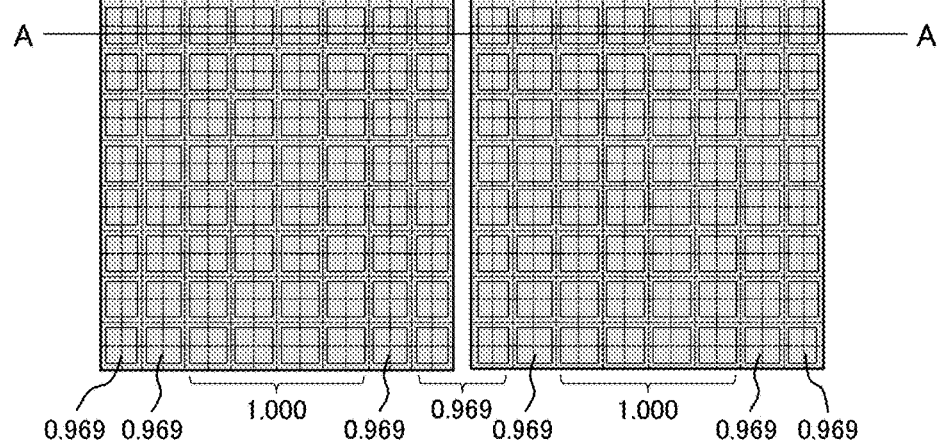
FIG. 10C
FIG. 10D
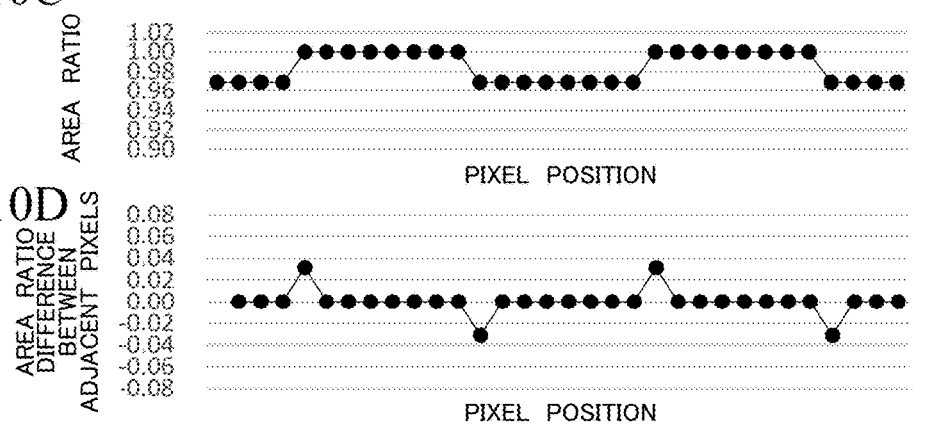

RADIOGRAPHIC IMAGING APPARATUS AND RADIATION DETECTOR

CLAIM OF PRIORITY

The present application claims priority from Japanese Patent Application JP 2021-146032 filed on Sep. 8, 2021, the content of which is hereby incorporated by reference into this application.

BACKGROUND OF THE INVENTION

The present invention relates to a radiographic imaging apparatus equipped with a photon counting detector and, more particularly, to a reduction in sensitivity difference between pixels of the photon counting detector.

The photon counting detector counts individual photons of incident radiation and measures energy for each photon. Therefore, a photon counting CT (Computed Tomography) apparatus equipped with the photon counting detector is capable of obtaining more information as compared with conventional CT apparatus equipped with a charge integration detector.

The photon counting detector is configured with a plurality of modules each having a stack of a semiconductor layer in which electrical charges are generated depending on the energy of incident photons, and a photon counting circuit for counting the generated electric charges for each pixel, and the plurality of modules is arranged in a plane orthogonal to an incident direction of the radiation.

Although the pixels in the module are arranged with a constant pitch, a gap is created between modules arranged in the same plane, so that the pixel pitch changes in a boundary area between adjacent modules.

Japanese Unexamined Patent Application Publication No. 2002-311145 discloses that, for the purpose of maintaining the pixel pitch continuity in the boundary area between modules, a pixel located in the boundary area is formed in a smaller size than a pixel located elsewhere than in the boundary area, and an output signal of the pixel in the boundary area is corrected depending on (pixel size)×(aperture ratio).

In Japanese Unexamined Patent Application Publication No. 2002-311145, however, adequate consideration is not given to the sensitivity difference between pixels resulting from the different pixel sizes. The photon counting circuit has dead time that is the time from when one photon is counted until when the next photon is to be counted. Therefore, as the incident photon rate which is the number of incident photons in a unit time is higher, the sensitivity is lower, so that the correction for an output signal depending on a ratio of pixel sizes is an inadequate approach. In another possible approach, the gap between modules can be narrowed to reduce the amount of reduction in pixel size in the boundary area. However, narrowing the gap between modules is impractical in terms of tolerance design. Such tolerance design will cause interference of modules, which in turn makes the arrangement impossible.

SUMMARY OF THE INVENTION

It is accordingly an object of the present invention to provide a radiographic imaging apparatus and a radiation detector which are capable of sufficiently reducing the sensitivity difference between pixels even if the incident photon rate is high.

To achieve the above object, an aspect of the present invention provides a radiographic imaging apparatus that includes: a radiation source for irradiating an object with radiation; a plurality of detection element modules each having a semiconductor layer that generates electrical charges depending on photon energy of the radiation, and a photon counting circuit for counting the electrical charges for each pixel; and a collimator that is disposed between the radiation source and the semiconductor layer, and has a plurality of walls forming a plurality of passage holes through which the radiation passes. A plurality of subpixels is formed on the semiconductor layer, and when one or more subpixels defined by the walls of the collimator are grouped as a macro pixel, a plurality of macro pixels arranged from each end of each of the detection element modules is smaller in size than a macro pixel other than the plurality of macro pixels arranged from the end of the detection element module.

Another aspect of the present invention provides a radiation detector that includes: a plurality of detection element modules each having a semiconductor layer that generates electrical charges depending on photon energy of radiation emitted to an object from a radiation source, and a photon counting circuit for counting the electrical charges for each pixel; and a collimator that is disposed between the radiation source and the semiconductor layer, and has a plurality of walls forming a plurality of passage holes through which the radiation passes. A plurality of subpixels is formed on the semiconductor layer, and when one or more subpixels defined by the walls of the collimator are grouped as a macro pixel, a plurality of macro pixels arranged from each end of each of the detection element modules is smaller in size than a macro pixel other than the plurality of macro pixels arranged from the end of the detection element module.

According to the present invention, it is possible to provide a radiographic imaging apparatus and a radiation detector which are capable of sufficiently reducing the sensitivity difference between pixels even if the incident photon rate is high.

BRIEF DESCRIPTION OF THE DRAWINGS

FIGS. 9A-9D are diagrams illustrating pixel sizes and an area ratio between adjacent pixels of a photon counting detector according to a fourth embodiment; and FIGS. 10A-10D are diagrams illustrating pixel sizes and an area ratio between adjacent pixels of a photon counting detector according to a fifth embodiment.

DETAILED DESCRIPTION OF THE PREFERRED EMBODIMENTS

Embodiments according to the present invention will now be described with reference to the accompanying drawings. A radiographic imaging apparatus according to the present invention is applied to an apparatus including a radiation source and a photon counting detector. The following description provides an example where radiation is X rays and the radiographic imaging apparatus is an X-ray CT apparatus.

First Embodiment

Figure 1:
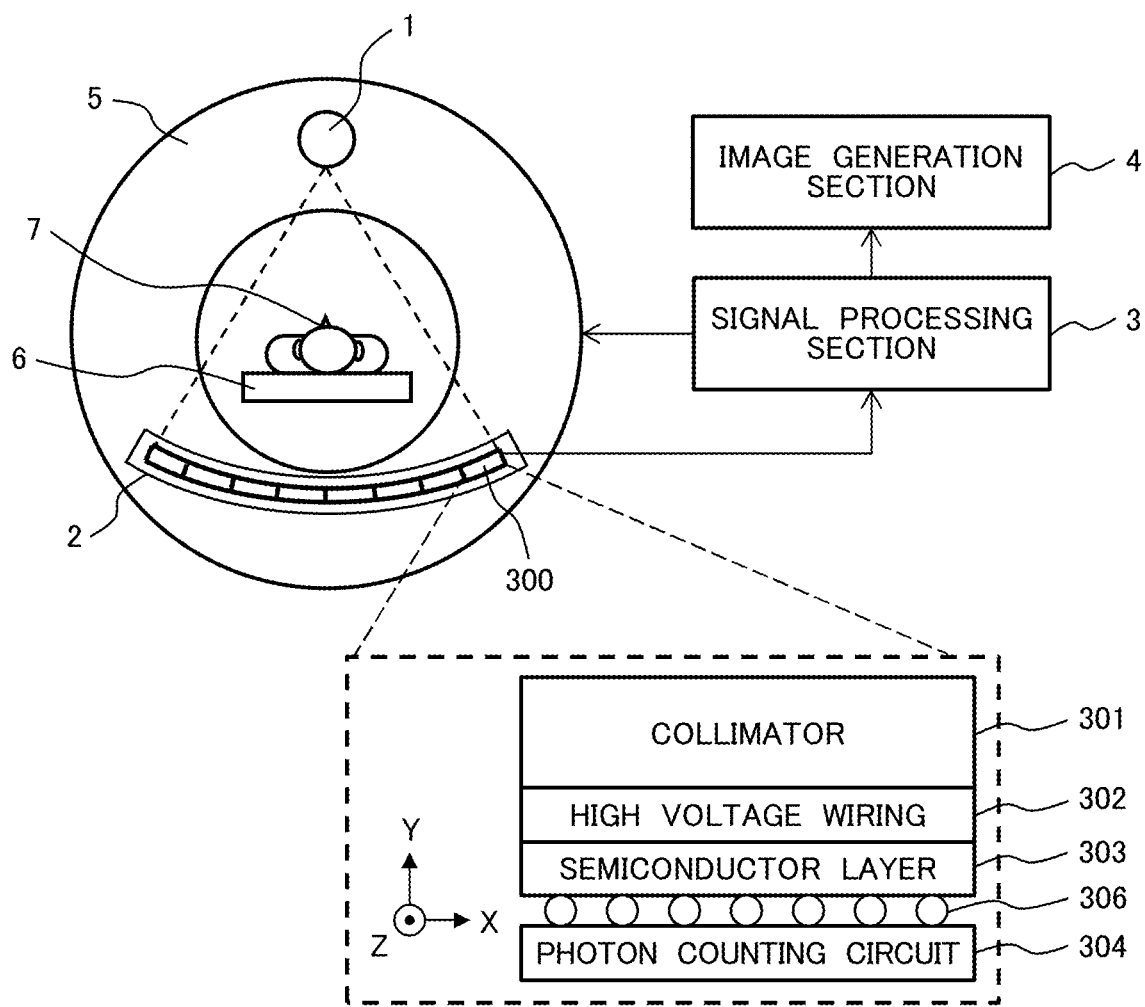
FIG. 1 is an overall configuration diagram of an X-ray CT apparatus to which the present invention is applied.

As illustrated in FIG. 1, an X-ray CT apparatus according to a first embodiment includes: an X ray source 1 for irradiating an object 7 with X rays; an X-ray detector 2 including a plurality of detection elements two-dimensionally arranged to detect X-ray photons; a signal processing section 3; and an image generation section 4. In the detection elements, pixels are two-dimensionally configured as units of photon counting. The signal processing section 3 performs processing for correction and/or the like on a detection signal output from the detection elements and controls each part of the X-ray CT apparatus. The image generation section 4 generates an image of the object 7 using the signal processed for correction and/or the like by the signal processing section 3. The X-ray source 1 and the X-ray detector 2 are configured to be supported on the opposite sides from each other by a rotating plate 5 to rotate around and relative to the object 7 laid on a bed 6.

The X-ray detector 2 is configured to include a plurality of detection element modules 300 arranged in an arc shape about the X-ray source 1. Each of the detection element modules 300 is a photon counting detector and has a collimator 301, high voltage wiring 302, a semiconductor layer 303, and a photon counting circuit 304. In FIG. 1, the Z axis is a direction of the rotating axis of the rotating plate 5, the Y axis is a direction of X-ray irradiation, and the X axis is a direction perpendicular to the YZ plane. Stated another way, the detection element modules 300 arranged in an arc shape have individually different Y and X axes.

The semiconductor layer 303 is made of, for example, cadmium zinc telluride (CZT), cadmium telluride (CdTe) and/or the like, and generates electric charges equivalent to the incident photon energy. The photon counting circuit 304 is connected to the semiconductor layer 303 through a plurality of pixel electrodes 306. The photon counting circuit 304 counts electric charges generated in the semiconductor layer 303 for each pixel, and outputs the count result as a count signal. The collimator 301 is a slit or grid formed of heavy metals such as tungsten and molybdenum, and minimize the scattered rays entering the semiconductor layer 303. The high voltage wiring 302 supplies high voltage to the semiconductor layer 303 to produce an electric filed field between the semiconductor layer 303 and the pixel electrodes 306. Due to the electric field thus produced, the electric charges generated in the semiconductor layer 303 move to the photon counting circuit 304 via the nearest pixel electrodes 306. Stated another way, a region in which electric charges moving to the pixel electrode 306 are generated corresponds to a pixel.

While the X-ray source 1 and the X-ray detector 2 that are located opposite each other are rotating around the object 7, the X-ray irradiation from the X-ray source 1 and the detection of X rays passing through the object 7 by the X-ray detector 2 are repeated. The count signals output by the photon counting circuits 304 of the X-ray detector 2 are processed for correction and/or the like at the signal processing section 3, and then transmitted to the image generation section 4. The image generation section 4 generates a tomographic image, i.e., CT image of the object 7 based on the received signals. For ensuring the image quality of the CT image, the photon counting circuit 304 is required to have uniform sensitivity.

Figure 2:
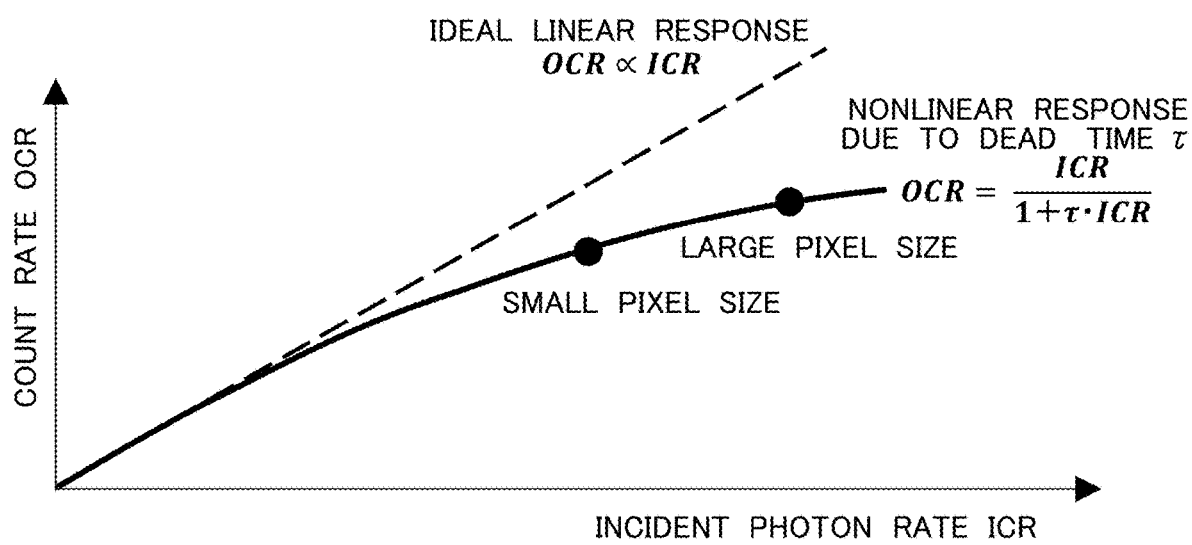
FIG. 2 is a graph illustrating an example of input-output characteristics of a photon counting circuit.

With reference to FIG. 2, an example of input-output characteristics of the photon counting circuit 304 will be described. In the graph of FIG. 2, the horizontal axis represents an incident photon rate ICR which is the number of photons entering the semiconductor layer 303 in a unit time, and the vertical axis represents a count rate OCR which is the number of photons counted by the photon counting circuit 304 in a unit time. Ideal input-output characteristics of the photon counting circuit 304 exhibit a linear response indicating constant sensitivity which is an OCR/ICR ratio between the incident photon rate ICR and the count rate OCR. However, since the photon counting circuit 304 has dead time τ that is the time from when one photon is counted until when the next photon is to be counted, the response is nonlinear such that as the incident photon rate is higher, the sensitivity is lower. Where the input-output characteristics exhibit a nonlinear response, even if the incident photon rate per unit area is the same, a sensitivity difference is made due to different pixel sizes. Thus, the correction for an output signal depending on a ratio of pixel sizes is an inadequate approach.

Figure 3A:
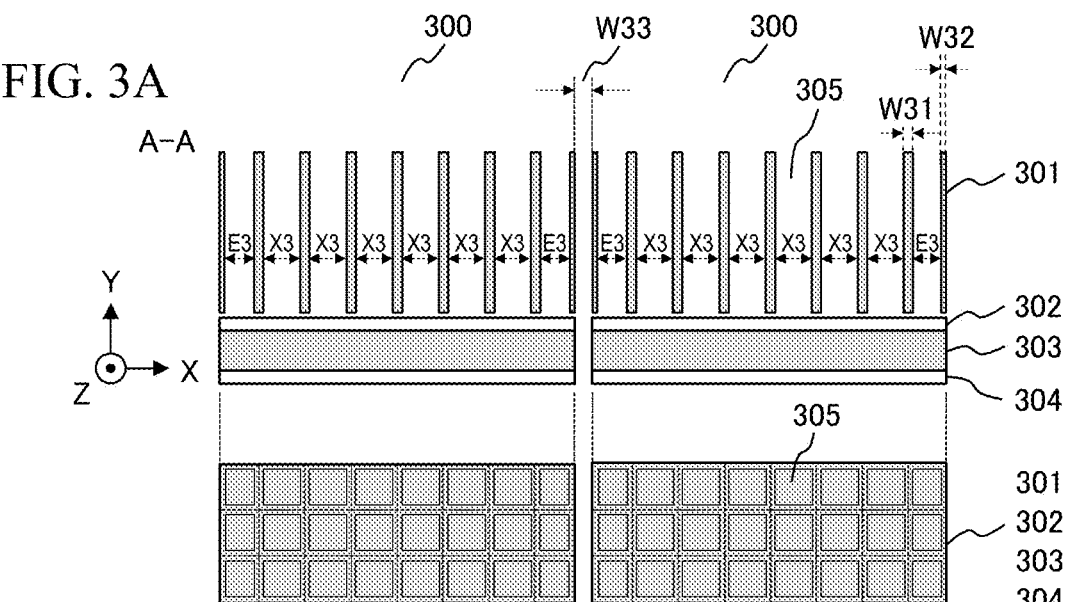
FIGS. 3A-3D are diagrams illustrating pixel sizes and an area ratio between adjacent pixels of a conventional photon counting detector.
Figure 3B:
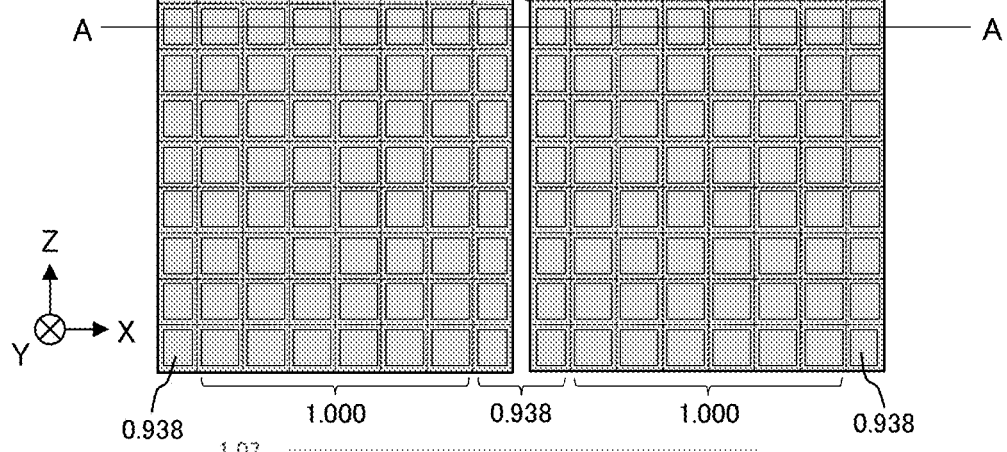

With reference to FIGS. 3A-3D, the pixel size and an area ratio between adjacent pixels of a conventional photon counting detector is described. FIG. 3A is a front view and FIG. 3B is a plan view of the detection element module 300. For example, the detection element module 300 has eight pixels arranged in the X direction and 16 pixels arranged in the Z direction, and also a gap W33 between detection element modules 300. In the semiconductor layer 303, pixels are two-dimensionally configured, and the pixels and apertures 305 of the collimator 301 are in the one-to-one correspondence, or alternatively, an N-to-one correspondence. Stated another way, the plurality of pixels is defined on the semiconductor layer by walls of the collimator 301, and is divided into groups each including one or more pixels. FIGS. 3A-3D show an example of a one-to-one correspondence, and FIGS. 9A-9D show an example of a four-to-one correspondence. In this manner, there exist two types of the pixels, the pixels configured on the semiconductor layer 303 and the pixels as the apertures 305. Therefore, for the purpose of a clear distinction between them, the pixel configured on the semiconductor layer 303 may be sometimes referred to as a subpixel, and the pixel defined by the aperture 305 may be sometimes referred to as a macro-pixel. The macro-pixel may be sometimes referred to simply as a pixel. It is noted that, in the case of the aforementioned one-to-one correspondence, the subpixel is equal to the macro-pixel. The collimator 301 has a wall thickness W32 at each end of the detection element module 300, and a wall thickness W31 elsewhere than at the ends. Further, a width of the aperture 305 between walls, i.e., a pixel size, is E3 in each end portion of the detection element module 300, and is X3 elsewhere than in the end portions. It is noted that the size E3 of a pixel in each end portion is smaller than the size X3 elsewhere than in the end portions, i.e., E3<X3, and E3=X3−W33/2.

Figure 3C:
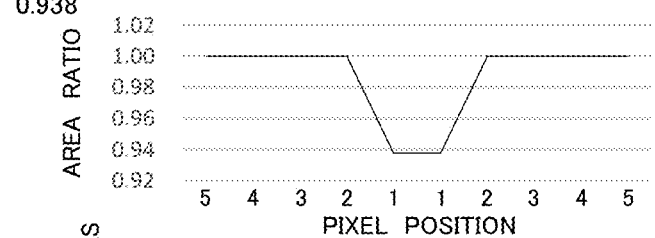
Figure 3D:
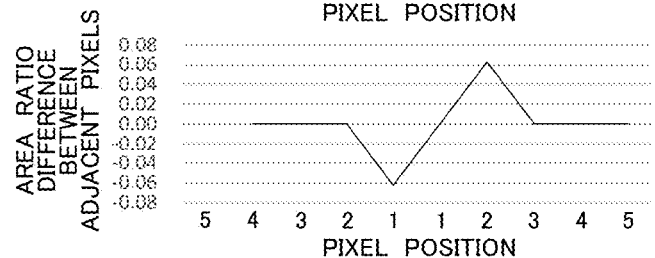

FIG. 3C illustrates an area ratio of pixels in proximity to the ends of the detection element module 300 when W31=0.2 mm, W32=0.1 mm, W33=0.1 mm, E3=0.75 mm, X3=0.8 mm, a pixel pitch in the X direction is 1 mm, and the pixels in the Z direction are of the same size. The area of a pixel in the end portion is 0.938 times the area of a pixel elsewhere than in the end portion. An absolute value of an area ratio difference between adjacent pixels illustrated in FIG. 3D is 0.06 or more. The area difference between pixels corresponds to a sensitivity difference of the photon counting detector. Therefore, the conventional photon counting detector has a sensitivity difference of 6% or more between adjacent pixels, making it difficult to ensure the image quality.

Figure 4A:
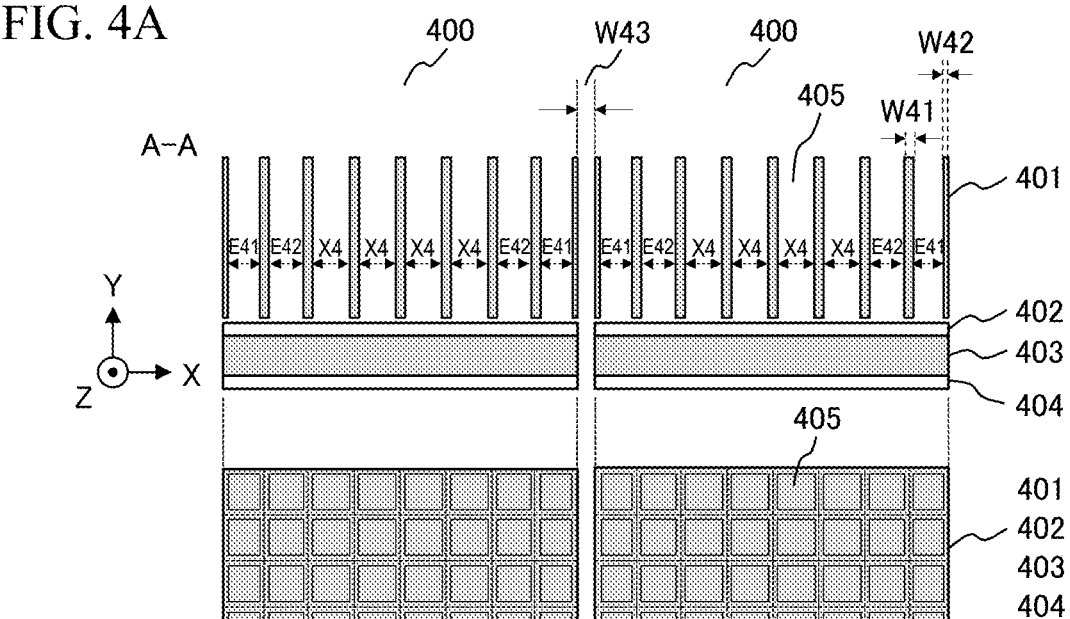
FIGS. 4A-4D are diagrams illustrating pixel sizes and an area ratio between adjacent pixels of a photon counting detector according to a first embodiment.
Figure 4B:
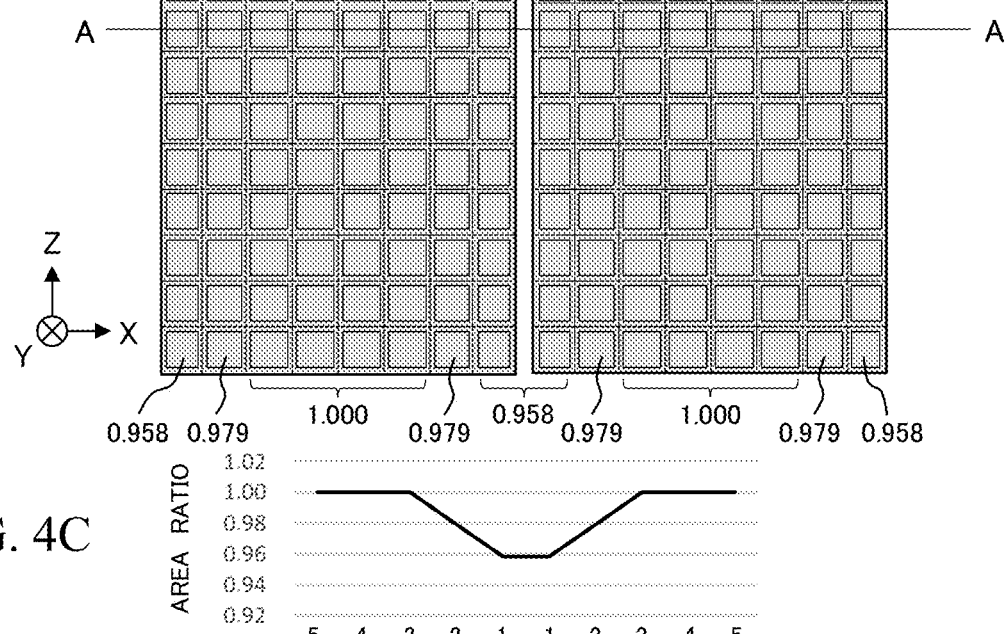

With reference to FIGS. 4A-4D, the pixel size and an area ratio between adjacent pixels of a photon counting detector according to a first embodiment will be described. FIG. 4A is a front view and FIG. 4B is a plan view of a detection element module 400. For example, the detection element module 400 has eight pixels arranged in the X direction and 16 pixels arranged in the Z direction, and also a gap W43 between detection element modules 400. A collimator 401 has a wall thickness W42 at ends of the detection element module 400, and a wall thickness W41 elsewhere than at the ends. Further, a width of an aperture 405 between walls, i.e., a pixel size, is E41 in each end portion of the detection element module 400, and is E42 in the portion adjacent thereto, and X4 elsewhere than in the end portions. It is noted that the size E41 of a pixel in each end portion and the size E42 of the pixel adjacent thereto are smaller than the size X4 of the remaining pixels, i.e., E41<E42<X4, and E41, E42, X4 form an arithmetic progression.

Figure 4C:
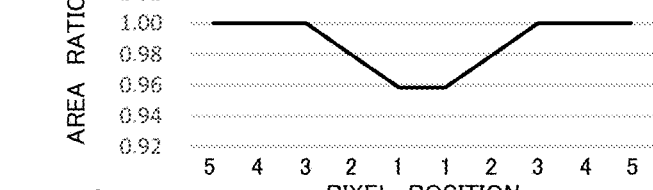
Figure 4D:
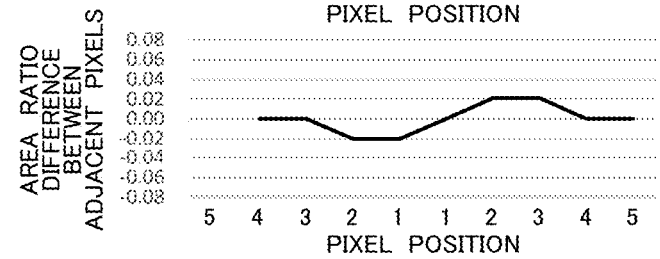

FIG. 4C illustrates an area ratio of pixels in proximity to the ends of the detection element module 400 when W41=0.2 mm, W42=0.1 mm, W43=0.1 mm, E41=0.767 mm, E42=0.783 mm, and X4=0.8 mm. For reference, a pixel pitch in the X direction is 1 mm and the pixels in the Z direction are of the same size. The area of the pixel in the end portion and the area of the pixel adjacent to thereto are respectively 0.958 and 0.979 times the area of the remaining pixels. Since E41, E42, X4 form an arithmetic progression, an absolute value of an area ratio difference between adjacent pixels illustrated in FIG. 4D is approximately 0.02 or less, which can be reduced to approximately one third of the conventional area ratio difference.

As described above, in the detection element module 400 illustrated in FIGS. 4A-4D, since the two pixels from each end are smaller in size than the remaining pixels, the sensitivity difference between adjacent pixels can be smaller than that in the conventional one. Since the sizes of the pixels arranged from the end form an arithmetic progression, the area ratio difference between adjacent pixels is smaller and thus the sensitivity difference between adjacent pixels may be sufficiently reduced. It will be apparent that the number of pixels reduced in size is not limited to two.

Figure 5A:
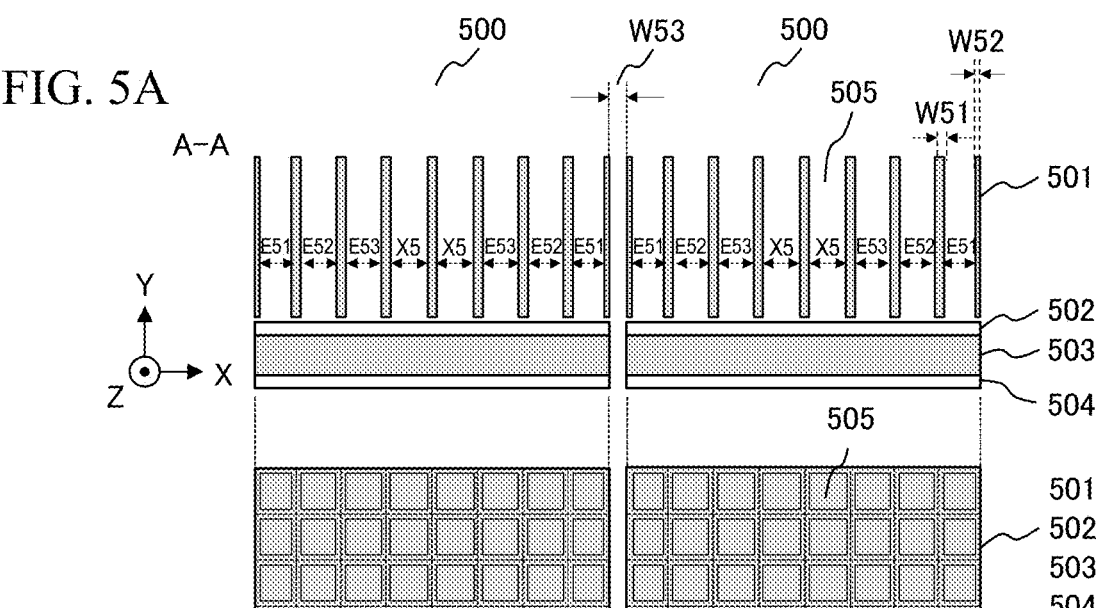
FIGS. 5A-5D are diagrams illustrating pixel sizes and an area ratio between adjacent pixels of a photon counting detector according to the first embodiment.
Figure 5B:
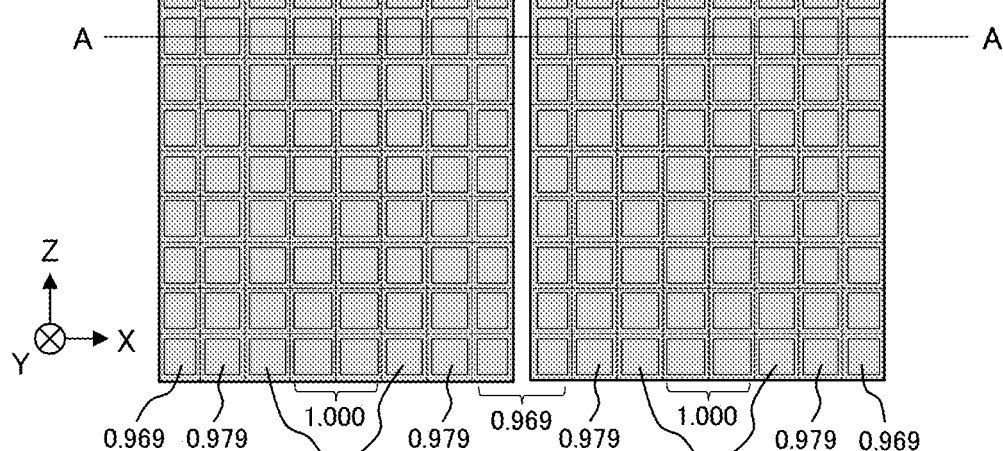

With reference to FIGS. 5A-5D, a description will be given of a photon counting detector in which the three pixels from each end are smaller in size than the remaining pixels. FIG. 5A is a front view and FIG. 5B is a plan view of a detection element module 500. For example, the detection element module 500 has eight pixels arranged in the X direction and 16 pixels arranged in the Z direction, and also a gap W53 between detection element modules 500. A collimator 501 has a wall thickness W52 at each end of the detection element module 500 and a wall thickness W51 elsewhere than at the ends. Further, a width of an aperture 505 between walls. i.e., a pixel size, is E51 in each end portion of the detection element module 500, E52 in the portion adjacent thereto, E53 in the portion further adjacent thereto, and X5 in the remainder. It is noted that the sizes E51, E52 and E53 of the three pixels from each end are smaller than the size X5 of the remaining pixels, i.e., E51<E52<E53<X5, and E51, E52, E53, X5 form an arithmetic progression.

Figure 5C:
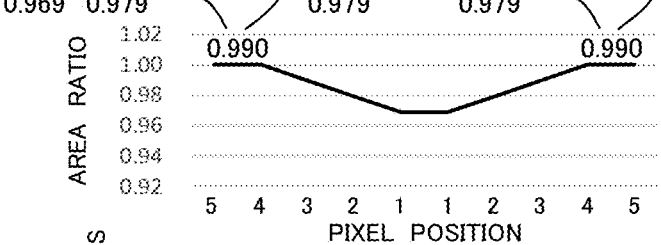
Figure 5D:
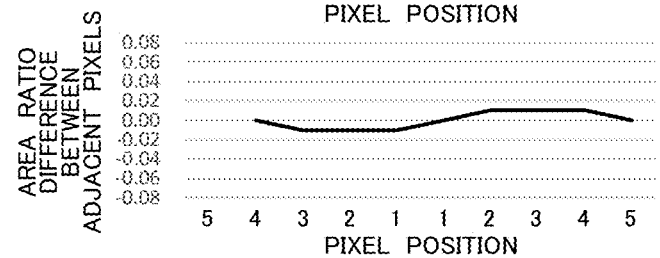

FIG. 5C illustrates an area ratio of pixels in proximity to the ends of the detection element module 500 when W51=0.2 mm, W52=0.1 mm, W53=0.1 mm, E51=0.775 mm, E52=0.783 mm, E53=0.792, and X5=0.8 mm. For reference, a pixel pitch in the X direction is 1 mm and the pixels in the Z direction are of the same size. The areas of the three pixels from each end are respectively 0.969, 0.979 and 0.990 times the area of the remaining pixels. Since E51, E52, E53, X5 form an arithmetic progression, an absolute value of an area ratio difference between adjacent pixels illustrated in FIG. 5D is approximate 0.01 or less, which can be reduced to approximately one sixth of the conventional area ratio difference.

As described above, in the detection element module 500 illustrated in FIGS. 5A-5D, since the three pixels from each end are smaller in size than the remaining pixels, the sensitivity difference between pixels can be smaller than that in the conventional one. Since the sizes of the pixels arranged from the end form an arithmetic progression, the area ratio difference between adjacent pixels is smaller and thus the sensitivity difference between adjacent pixels may be sufficiently reduced.

When n pixels from each end are smaller in size than the remaining pixels, and the sizes of the pixels arranged from the end form an arithmetic progression, a difference $\Delta$ of the arithmetic progression may be calculated from the following equation.

$$\Delta = W/(n \cdot (n+1)) \tag{Eq. 1}$$

where W is a gap between detection element modules, and $n \geq 2$.

Second Embodiment

In the first embodiment, a description has been given of the configuration in which a plurality of pixels from each end of the detection element module is smaller in size than the remaining pixels, and the sizes of the pixels arranged from the end form an arithmetic progression. In a second embodiment, a description will be given of the configuration in which a plurality of pixels from each end of the detection element module is smaller in size than the remaining pixels and also the plurality of pixels from the end have a uniform size. It is noted that since the configuration and/or functions described in the first embodiment can be partially applied to the second embodiment, like reference signs are used to indicate similar configurations, functions and a description is omitted.

Figure 6A:
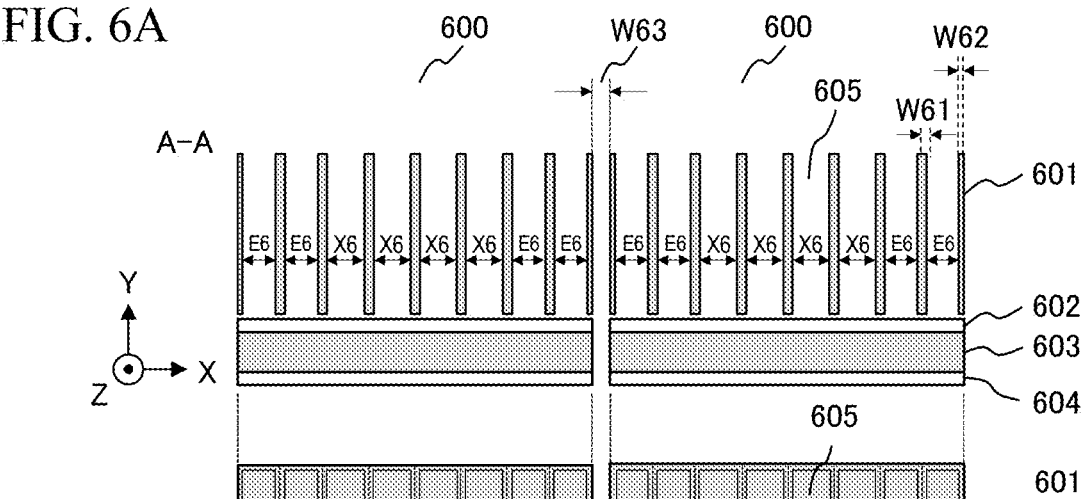
FIGS. 6A-6D are diagrams illustrating pixel sizes and an area ratio between adjacent pixels of a photon counting detector according to a second embodiment.
Figure 6B:
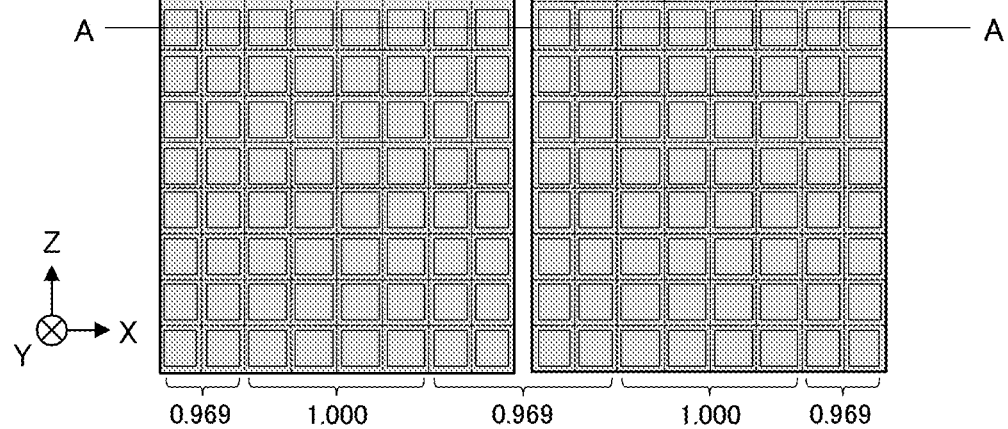

With reference to FIGS. 6A-6D, the pixel size and an area ratio between adjacent pixels of a photon counting detector according to the second embodiment will be described. FIG. 6A is a front view and FIG. 6B is a plan view of a detection element module 600. For example, the detection element module 600 has eight pixels arranged in the X direction and 16 pixels arranged in the Z direction, and also a gap W63 between detection element modules 600. A collimator 601 has a wall thickness W62 at each end of the detection element module 600, and a wall thickness W61 elsewhere than at the ends. Further, a width of an aperture 605 between walls, i.e., a pixel size, is E6 equally in each end portion and the portion adjacent thereto of the detection element module 600, and X6 in the remainder. It is noted that the size E6 of the pixel in each end portion and the pixel adjacent thereto is smaller than the size X6 of the remaining pixels, i.e., E6<X6.

Figure 6C:
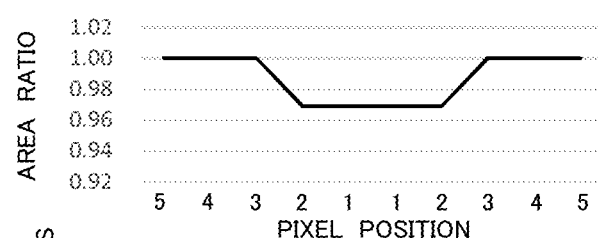
Figure 6D:
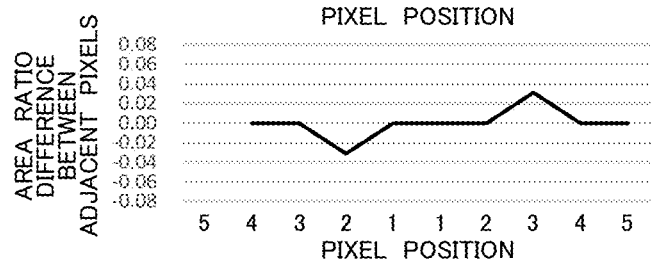

FIG. 6C illustrates an area ratio of pixels in proximity to the ends of the detection element module 600 when W61=0.2 mm, W62=0.1 mm, W63=0.1 mm, E6=0.775 mm, and X6=0.8 mm. For reference, a pixel pitch in the X direction is 1 mm and the pixels in the Z direction are of the same size. Both the area of the pixel in each end portion and the area of the pixel adjacent thereto are 0.969 times the area of the remaining pixels. An absolute value of an area ratio difference between adjacent pixels illustrated in FIG. 6D is approximately 0.03 or less, which can be reduced to approximately one half of the conventional area ratio difference.

As described above, in the detection element module 600 illustrated in FIGS. 6A-6D, since the two pixels from each end are smaller in size than the remaining pixels, the sensitivity difference between pixels can be smaller than that in the conventional one. Further, since a pixel in each end portion and the pixel adjacent thereto are equal in size to each other, the manufacture is facilitated. It will be apparent that the number of pixels reduced in size is not limited to two.

Figure 7A:
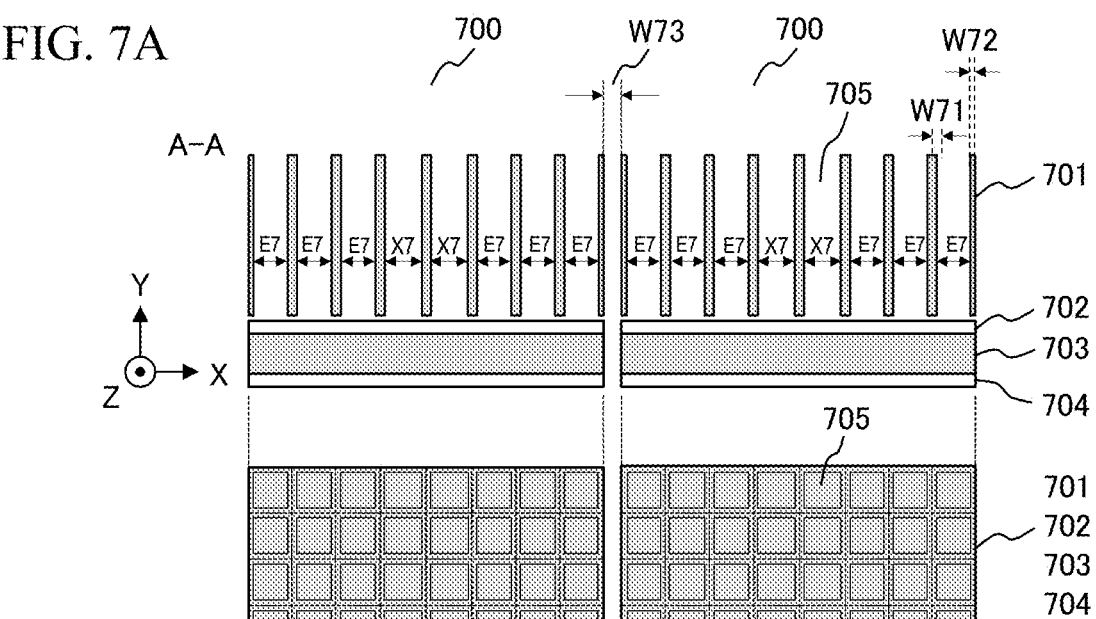
FIGS. 7A-7D are diagrams illustrating pixel sizes and an area ratio between adjacent pixels of a photon counting detector according to the second embodiment.
Figure 7B:
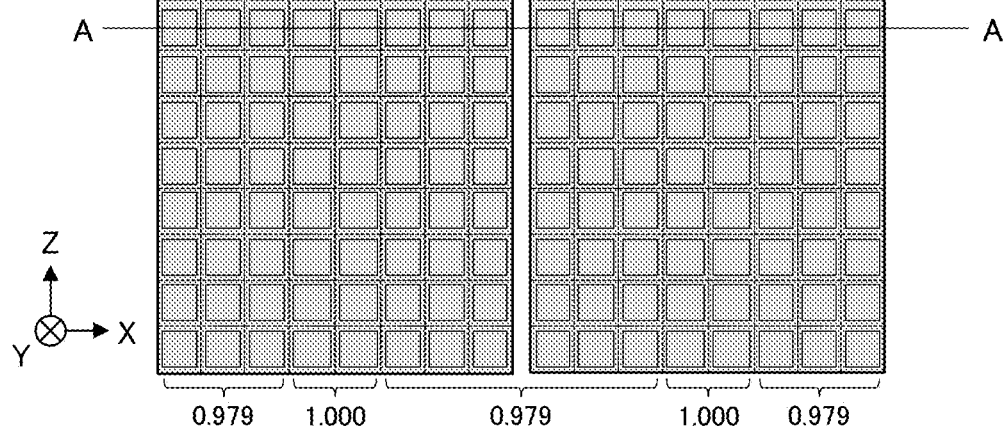

With reference to FIGS. 7A-7D, a description will be given of a photon counting detector in which the three pixels from each end are smaller in size than the remaining pixels. FIG. 7A is a front view and FIG. 7B is a plan view of a detection element module 700. For example, the detection element module 700 has eight pixels arranged in the X direction and 16 pixels arranged in the Z direction, and also a gap W73 between detection element modules 700. A collimator 701 has a wall thickness W72 at each end of the detection element module 700 and a wall thickness W71 elsewhere than at the ends. Further, a width of an aperture 705 between walls. i.e., a pixel size, is E7 equally in the three pixels from each end of the detection element module 700, and X7 in the remainder. It is noted that the size E7 of the three pixels from each end is smaller than the size X7 of the remaining pixels, i.e., E7<X7.

Figure 7C:
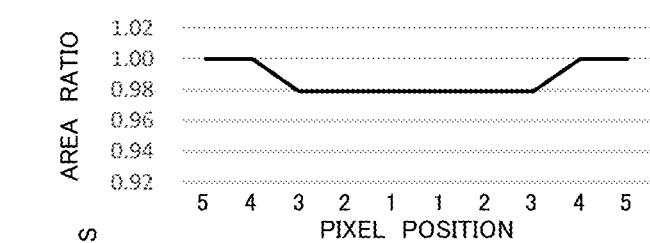
Figure 7D:
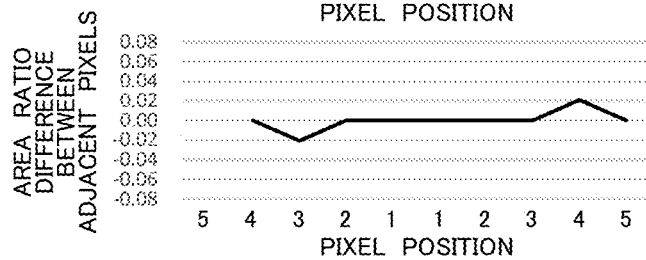

FIG. 7C illustrates an area ratio of pixels in proximity to the ends of the detection element module 700 when W71=0.2 mm, W72=0.1 mm, W73=0.1 mm, E7=0.783 mm, and X7=0.8 mm. For reference, a pixel pitch in the X direction is 1 mm and the pixels in the Z direction are of the same size. The area of each of the three pixels from each end are 0.979 times the area of the remaining pixels. An absolute value of an area ratio difference between adjacent pixels illustrated in FIG. 7D is approximately 0.02 or less, which can be reduced to approximately one third of the conventional area ratio difference.

As described above, in the detection element module 700 illustrated in FIGS. 7A-7D, since the three pixels from each end are smaller in size than the remaining pixels, the sensitivity difference between pixels can be smaller than that in the conventional one. Further, since the three pixels arranged from each end are uniform in size, the manufacture is facilitated.

When n pixels from each end are smaller in size than the remaining pixels and also uniform in size, the size E may be calculated from the following equation.

$$E=(X-W/2)/n \tag{Eq. 2}$$

where X is a size of pixels other than the n pixels from each end, W is a gap between detection element modules, and $n \geq 2$.

Third Embodiment

In the first embodiment, the case where a gap is created only between detection element modules has been described. As the semiconductor layer used in the detection element module has a larger area, the yield is reduced. Therefore, the manufacturing cost can be reduced by using a semiconductor layer with a smaller area. In a third embodiment, a description will be given of the case where a gap is also created inside the detection element module for use of a semiconductor layer with a smaller area. It is noted that since the configuration and/or functions described in the first embodiment can be partially applied to the third embodiment, like reference signs are used to indicate similar configurations, functions and a description is omitted.

Figure 8A:
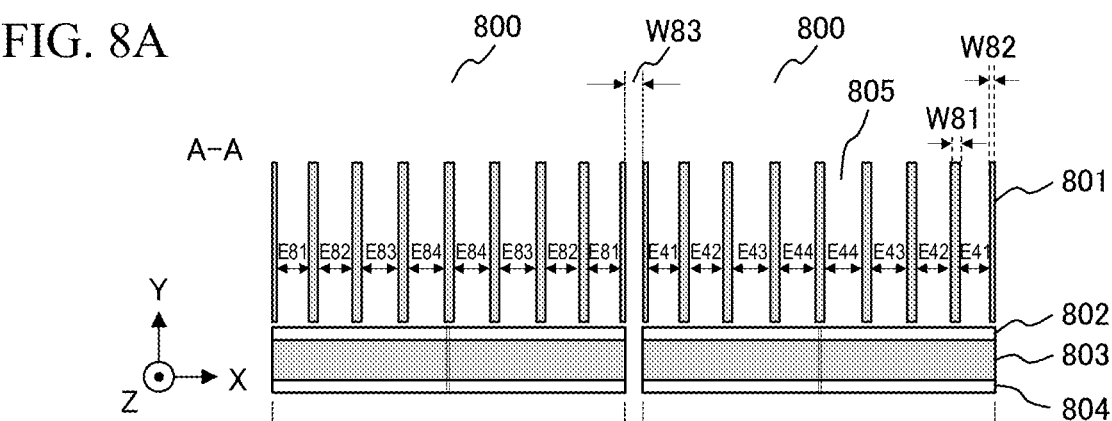
FIGS. 8A-8D are diagrams illustrating pixel sizes and an area ratio between adjacent pixels of a photon counting detector according to a third embodiment.
Figure 8B:
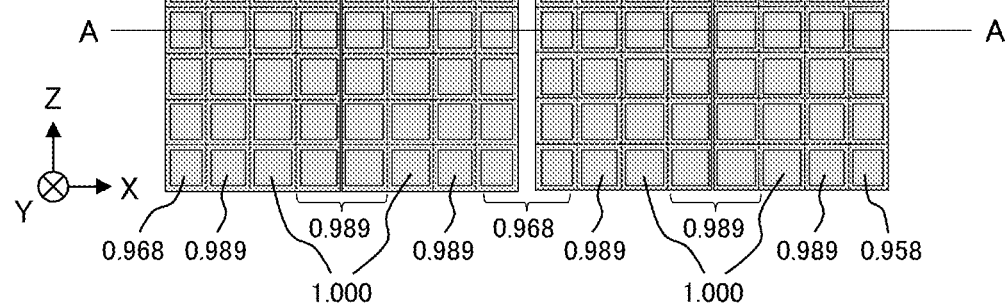

With reference to FIGS. 8A-8D, the pixel size and an area ratio between adjacent pixels of a photon counting detector according to the third embodiment will be described. FIG. 8A is a front view and FIG. 8B is a plan view of a detection element module 800. For example, the detection element module 800 has eight pixels arranged in the X direction and eight pixels arranged in the Z direction, and also has a gap W83 between detection element modules 800 and a gap W84 inside the detection element module 800. Specifically, within the detection element module 800, the high voltage wiring 802, the semiconductor layer 803, and the photon counting circuit 804 are divided into two in the X direction. A collimator 801 has a wall thickness W82 at each end of the detection element module 800 and a wall thickness W81 elsewhere than at the ends. Further, the widths of apertures 805 between walls. i.e., pixel sizes, are E81, E82, E83, E84, E84, E83. E82, and E81 that are arranged in this order in the X direction. It is noted that the sizes E81, E82 of the two pixels from each end are smaller than the size E83 of the pixel adjacent thereto, i.e., E81<E82<E83, and E81, E82, E83 form an arithmetic progression. Further, the size E84 of the pixel adjacent to the gap W84 inside the detection element module 800 is smaller than the size E83 of the pixel adjacent thereto.

Figure 8C:
Figure 8D:
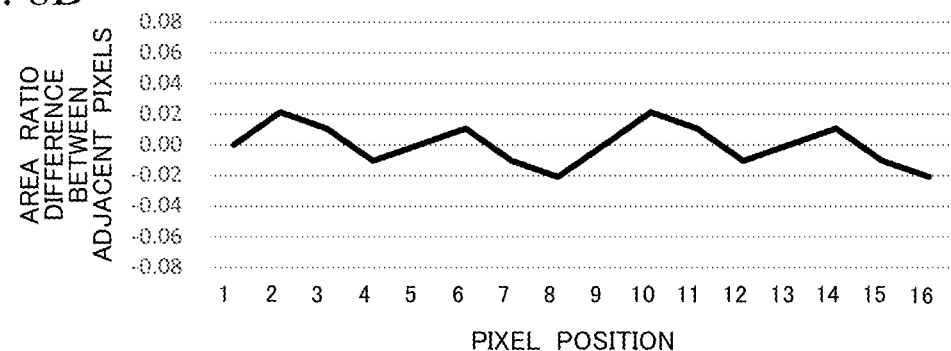

FIG. 8C illustrates an area ratio of pixels in proximity to the ends when W81=0.2 mm, W82=0.1 mm, W83=0.1 mm, W84=0.050 mm, E81=0.767 mm, E82=0.783 mm, E83=0.792 mm, and E84=0.783 mm. For reference, a pixel pitch in the X direction is 1 mm and the pixels in the Z direction are of the same size. The areas of the respective pixels are 0.968, 0.989, 1.000, 0.989, 0.989, 1.000, 0.989, and 0.968 times the area of the pixel size E83 of the pixel with the maximum area. Since E81, E82, and E83 form an arithmetic progression, an absolute value of an area ratio difference between adjacent pixels illustrated in FIG. 8D is approximately 0.02 or less, which can be reduced to approximately one third of the conventional area ratio difference.

As described above, in the detection element module 800 illustrated in FIGS. 8A-8D, since the two pixels from each end are smaller in size than the remaining pixels, the sensitivity difference between pixels can be smaller than that in the conventional one. Further, since the sizes of the two pixels arranged from the end form an arithmetic progression, the area ratio difference between adjacent pixels is smaller, so that the sensitivity difference between adjacent pixels may be sufficiently reduced. Further, the size of the pixel adjacent to the internal gap inside the detection element module 800 is smaller than that of the pixel adjacent thereto, thereby maintaining the pixel pitch and enabling using a semiconductor layer with a smaller area. As a result, a reduction in manufacturing cost can be achieved.

Fourth Embodiment

In the first embodiment, the case where the subpixels and the macro pixels are in the one-to-one correspondence has been described. In a fourth embodiment, the case where the subpixels and the macro pixels are in the four-to-one correspondence will be described. The counting performance is improved by dividing each pixel into a plurality of subpixels. It is noted that since the configuration and/or functions described in the first embodiment can be partially applied to the fourth embodiment, like reference signs are used to indicate similar configurations, functions and a description is omitted.

With reference to FIGS. 9A-9D, the pixel size and an area ratio between adjacent pixels of a photon counting detector according to the fourth embodiment will be described. FIG. 9A is a front view and FIG. 9B is a plan view of a detection element module 900. For example, the detection element module 900 has eight pixels arranged in the X direction and 16 pixels arranged in the Z direction, and also has a gap W93 between detection element modules 900. Further, each pixel is divided into 2 by 2 subpixels. A collimator 901 has a wall thickness W92 at each end of the detection element module 900 and a wall thickness W91 elsewhere than at the ends. Further, the width of aperture 905 between walls. i.e., pixel size, is E91 in each end portion of the detection element module 900, E92 in the portion adjacent thereto, and X9 in the remainder. Further, the subpixels in the pixel of pixel size E91 have size E911 and E912, and the subpixels in the pixel of size E92 have size E921 and E922. It is noted that the sizes E91 and E92 of the pixel in the end portion and the pixel adjacent thereto are smaller than the size X9 of the remaining pixels, i.e., E91<E92<X9, and E911, E912, E921, E922, X9/2 form an arithmetic progression.

FIG. 9C illustrates an area ratio of subpixels in proximity to the ends when W91=0.2 mm, W92=0.1 mm, W93=0.1 mm, X9=0.800 mm, E911=0.380 mm, E912=0.385 mm, E921=0.390 mm, and E922=0.395 mm. For reference, a pixel pitch in the X direction is 1 mm and the pixels in the Z direction are of the same size. The areas of the subpixels of the pixel in the end potion and the pixel adjacent thereto are respectively 0.950, 0.963, 0.975, and 0.988 times the area of the subpixels of the remaining pixels. Further, since E911, E912, E921, E922, and X9/2 form an arithmetic progression, an absolute value of an area ratio difference between adjacent subpixels illustrated in FIG. 9D is approximately 0.013 or less, which can be reduced to approximately one fifth of the conventional area ratio difference. If a pixel is divided into a plurality of subpixels as illustrated in FIGS. 9A-9D, since a pixel electrode is installed for each subpixel, a higher degree of placement accuracy for the pixel electrodes is required. Therefore, it is inevitable that not only the pixels in the end portions of the detection element module as in the conventional photon counting detectors but also a plurality of pixels from the end is reduced in size to minimize the amount of size reduction per pixel.

As described above, in the detection element module 900 illustrated in FIGS. 9A-9D, since the subpixels of the two pixels from each end are smaller in size than the subpixels of the remaining pixels, the sensitivity difference between pixels can be smaller than that in the conventional one. Further, since the sizes of the subpixels of the two pixels from the end form an arithmetic progression, the area ratio difference between adjacent subpixels is smaller, so that the sensitivity difference between adjacent subpixels may be sufficiently reduced. Further, each pixel of the detection element module 900 is divided into the subpixels, so that the counting performance can be improved.

Fifth Embodiment

In the fourth embodiment, a description has been given of the case where the subpixels and the macro pixels are in the four-to-one correspondence and also the areas of the subpixels in each end portion are set to form an arithmetic progression. In a fifth embodiment, a description will be given of the case where the areas of the subpixels are not in the arithmetic progression and the subpixels are set to have approximately the same area. Setting the subpixels to have approximately the same area produces effects of facilitating the design and verification as well as of stabilizing the manufacturing process. It is noted that since the configuration and/or functions described in the first embodiment can be partially applied to the fifth embodiment, like reference signs are used to indicate similar configurations, functions and a description is omitted.

With reference to FIGS. 10A-10D, the pixel size and an area ratio between adjacent pixels of a photon counting detector according to the fifth embodiment will be described. FIG. 10A is a front view and FIG. 10B is a plan view of a detection element module 1000. For example, the detection element module 1000 has eight pixels arranged in the X direction and 16 pixels arranged in the Z direction, and also has a gap W103 between detection element modules 1000. Further, each pixel is divided into 2 by 2 subpixels. A collimator 1001 has a wall thickness W102 at each end of the detection element module 1000 and a wall thickness W101 elsewhere than at the ends. Further, the width of an aperture 1005 between walls. i.e., pixel size, is E101 in each end portion and the portion adjacent thereto of the detection element module 1000, and X10 in the remainder. Further, the subpixels in the pixels of size E101 have size E1011. It is noted that the size E101 of the pixel in the end portion and the pixel adjacent thereto are smaller than the size X10 of the remaining pixels.

FIG. 10C illustrates an area ratio of subpixels in proximity to the ends when W101=0.2 mm, W102=0.1 mm, W103=0.1 mm, X10=0.800 mm, and E1011=0.3775 mm. For reference, a pixel pitch in the X direction is 1 mm and the pixels in the Z direction are of the same size. The area of all the subpixels of the pixel in the end potion and the pixel adjacent thereto are 0.969 times the area of the subpixels of the remaining pixels. Further, an absolute value of an area ratio difference between adjacent subpixels illustrated in FIG. 10D is approximately 0.03 or less, which can be reduced to approximately one half of the conventional area ratio difference. If a pixel is divided into a plurality of subpixels as illustrated in FIGS. 10A-10D, since a pixel electrode is required to be installed for each subpixel, more severe dimensional restrictions on pixels are introduced for the placement of the pixel electrodes. Therefore, it is inevitable that not only the dimensions of pixels in the module end portions as in the conventional techniques but also a plurality of pixels from the module end is reduced in dimensions to minimize the amount of dimension reduction per pixel.

As described above, in the detection element module 1000 illustrated in FIGS. 10A-10D, since the subpixels of the two pixels from each end are smaller in size than the subpixels of the remaining pixels, the sensitivity difference between pixels can be smaller than that in the conventional one. Further, since the subpixels of the two pixels from the end are equal in size, the manufacturing is facilitated. It will be apparent that the number of pixels reduced in size is not limited to two.

A plurality of embodiments of the radiographic imaging apparatus according to the present invention has been described. The radiographic imaging apparatus according to the present invention is not limited to the above embodiments, and may be embodied by modifying components thereof without departing from the spirit or scope of the present invention. For example, the pixel pitch in the X direction may not necessarily be the same, and a gap between detection element modules may be increased without any change in size of the plurality of pixels from the end. Further, a plurality of components disclosed in the above embodiments may be combined as appropriate. Further, several components of all the components described in the above embodiments may be omitted.

REFERENCE SIGNS LIST

1 . . . X-ray source
2 . . . X-ray detector
3 . . . signal processing section
4 . . . image generation section
5 . . . rotating plate
6 . . . bed
7 . . . object
300 . . . detection element module
301 . . . collimator
302 . . . high voltage wiring
303 . . . semiconductor layer
304 . . . photon counting circuit
305 . . . aperture
306 . . . pixel electrode
400 . . . detection element module
401 . . . collimator
402 . . . high voltage wiring
403 . . . semiconductor layer
404 . . . photon counting circuit
405 . . . aperture
500 . . . detection element module
501 . . . collimator
502 . . . high voltage wiring
503 . . . semiconductor layer
504 . . . photon counting circuit
505 . . . aperture
600 . . . detection element module
601 . . . collimator
602 . . . high voltage wiring
603 . . . semiconductor layer
604 . . . photon counting circuit
605 . . . aperture
700 . . . detection element module
701 . . . collimator
702 . . . high voltage wiring
703 . . . semiconductor layer
704 . . . photon counting circuit
705 . . . aperture
800 . . . detection element module
801 . . . collimator
802 . . . high voltage wiring
803 . . . semiconductor layer
804 . . . photon counting circuit
805 . . . aperture
900 . . . detection element module
901 . . . collimator
902 . . . high voltage wiring
903 . . . semiconductor layer
904 . . . photon counting circuit
905 . . . aperture
1000 . . . detection element module
1001 . . . collimator
1002 . . . high voltage wiring
1003 . . . semiconductor layer
1004 . . . photon counting circuit
1005 . . . aperture

What is claimed is:

1. A radiographic imaging apparatus, comprising:
a radiation source for irradiating an object with radiation;
a plurality of detection element modules, each detection element module having a semiconductor layer that generates electrical charges depending on photon energy of the radiation, and a photon counting circuit for counting the electrical charges for each pixel; and
a collimator that is disposed between the radiation source and the semiconductor layer, and has a plurality of walls forming a plurality of passage holes through which the radiation passes, wherein
a plurality of subpixels is formed on the semiconductor layer, and
one or more subpixels defined by the walls of the collimator are grouped as a macro pixel, and
each of a plurality of macro pixels arranged from a macro pixel adjacent to a gap between the detection element modules is smaller in size than a macro pixel other than the plurality of macro pixels and the macro pixel adjacent to the gap.

2. The radiographic imaging apparatus according to claim 1, wherein the macro pixels arranged from the end of the detection element module have sizes forming an arithmetic progression.

3. The radiographic imaging apparatus according to claim 2, wherein a difference Δ of the arithmetic progression is calculated as Δ=W/(n·(n+1)), where n is the number of macro pixels of a smaller size and W is a gap between the detection element modules.

4. The radiographic imaging apparatus according to claim 1, wherein the macro pixels arranged from the end of the detection element module are uniform in size.

5. The radiographic imaging apparatus according to claim 4, wherein the macro pixels arranged from the end of the detection element module have a size E that is calculated as E=(X−W/2)/n, where n is the number of macro pixels of a smaller size, W is a gap between the detection element modules, and X is a size of a macro pixel other than the macro pixels of the size E.

6. The radiographic imaging apparatus according to claim 1, wherein if there is an internal gap which is a gap inside the detection element module, a macro pixel located adjacent to the internal gap has a size smaller than that of a macro pixel adjacent to the macro pixel.

7. The radiographic imaging apparatus according to claim 1, wherein the subpixels forming the plurality of macro pixels of smaller sizes located close to the end of the detection element module are reduced in size toward the end in arithmetic progression.

8. The radiographic imaging apparatus according to claim 1, wherein the subpixels forming the plurality of macro pixels of smaller sizes located close to the end of the detection element module are uniform in size.

9. A radiation detector, comprising:
a plurality of detection element modules, each detection element module having a semiconductor layer that generates electrical charges depending on photon energy of radiation emitted to an object from a radiation source, and a photon counting circuit for counting the electrical charges for each pixel; and
a collimator that is disposed between the radiation source and the semiconductor layer, and has a plurality of walls forming a plurality of passage holes through which the radiation passes, wherein
a plurality of subpixels is formed on the semiconductor layer, and
one or more subpixels defined by the walls of the collimator are grouped as a macro pixel, and
each of a plurality of macro pixels arranged from a macro pixel adjacent to a gap between the detection element modules is smaller in size than a macro pixel other than the plurality of macro pixels and the macro pixel adjacent to the gap.

10. The radiation detector according to claim 9, wherein the macro pixels arranged from the end of the detection element module have sizes forming an arithmetic progression.

11. The radiation detector according to claim 10, wherein a difference $\Delta$ of the arithmetic progression is calculated as $\Delta = W/(n \cdot (n+1))$, where n is the number of macro pixels of a smaller size and W is a gap between the detection element modules.

12. The radiation detector according to claim 9, wherein the macro pixels arranged from the end of the detection element module are uniform in size.

13. The radiation detector according to claim 12, wherein the macro pixels arranged from the end of the detection element module have a size E that is calculated as $E = (X - W/2)/n$, where n is the number of macro pixels of a smaller size, W is a gap between the detection element modules, and X is a size of a macro pixel other than the macro pixels of the size E.

14. The radiation detector according to claim 9, wherein if there is an internal gap which is a gap inside the detection element module, a macro pixel located adjacent to the internal gap has a size smaller than that of a macro pixel adjacent to the macro pixel.

15. The radiation detector according to claim 9, wherein the subpixels forming the plurality of macro pixels of smaller sizes located close to the end of the detection element module are reduced in size toward the end in arithmetic progression.

16. The radiation detector according to claim 9, wherein the subpixels forming the plurality of macro pixels of smaller sizes located close to the end of the detection element module are uniform in size.

* * * * *